United States Patent [19]

Tsuboniwa et al.

[11] Patent Number: 5,434,296

[45] Date of Patent: Jul. 18, 1995

[54] PROCESS FOR PRODUCING UNSATURATED CARBAMIC ACID ESTERS

[75] Inventors: Noriyuki Tsuboniwa, Higashiosaka; Eiji Yamanaka, Suita; Satoshi Urano, Tsuzuki, all of Japan

[73] Assignee: Nippon Paint Co., Ltd., Osaka, Japan

[21] Appl. No.: 193,651

[22] Filed: Feb. 7, 1994

Related U.S. Application Data

[60] Continuation of Ser. No. 952,643, Sep. 28, 1992, abandoned, which is a division of Ser. No. 723,271, Jun. 28, 1991, Pat. No. 5,187,306.

[30] Foreign Application Priority Data

Jul. 3, 1990 [JP] Japan .................. 2-177180

[51] Int. Cl.$^6$ ............................. C07C 261/00
[52] U.S. Cl. ................. 560/157; 549/496; 560/162; 560/163; 560/164
[58] Field of Search ............... 560/158, 162, 163, 164, 560/157; 549/496

[56] References Cited

U.S. PATENT DOCUMENTS

| | | | |
|---|---|---|---|
| 2,306,599 | 12/1942 | Engel | 560/157 |
| 3,819,683 | 6/1974 | Krebs | 560/157 |
| 4,001,191 | 1/1977 | Reed | 560/157 |
| 4,021,224 | 5/1977 | Pallos | 560/157 |
| 4,935,413 | 6/1990 | Urano | 560/157 |

FOREIGN PATENT DOCUMENTS 57-81477  5/1982  Japan .

OTHER PUBLICATIONS

Weygand, "Preparative Organic Chemistry," pp. 464–472 (1972).
"Hackh's Chemical Dictionary", 4th Ed., p. 35 (1969).

*Primary Examiner*—Michael L. Shippen
*Attorney, Agent, or Firm*—Wenderoth, Lind & Ponack

[57] ABSTRACT

The present invention provides a manufacturing method for unsaturated carbamic acid esters by allowing an unsaturated amide compound to react with a metallic base in an inert solvent, followed by a reaction with a halogenated formic acid ester.

The invention also provides a manufacturing method of unsaturated carbamic acid esters by allowing an urethane derivative to react with a metallic base in an inert solvent, followed by a reaction with an unsaturated acid halide.

12 Claims, No Drawings

PROCESS FOR PRODUCING UNSATURATED CARBAMIC ACID ESTERS

This is a continuation application of Ser. No. 07/952,643, filed Sep. 28, 1992, now abandoned, which in turn is a divisional of application Ser. No. 07/723,271, filed Jun. 28, 1991, now U.S. Pat. No. 5,187,306.

FIELD OF THE INVENTION

The present invention relates to a novel process for producing unsaturated carbamic acid esters represented by the following general formula:

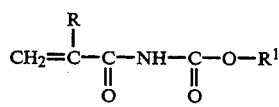
[I]

(wherein R denotes a hydrogen atom or a lower alkyl group and $R^1$ denotes a residue obtained by subtracting a hydroxyl group from a monohydric alcohol.)

BACKGROUND OF THE INVENTION

The inventors of the present invention have already developed unsaturated carbamic acid esters represented by the general formula below and the use applications thereof (Japanese Patent Laid-Open Publications No. 61-275259, 61-275260 and 61-275270):

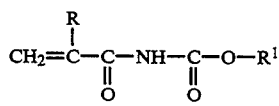
[I]

(wherein R and $R^1$ are the same as mentioned above.)

The unsaturated carbamic acid esters are produced, as are disclosed in the foregoing patent laid-open publications, by allowing the unsaturated amide compounds represented by a general formula (1) to react with the oxalyl chloride (where R and $R^1$ denote the same meanings as the ones to be described hereinafter)

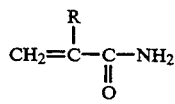
(1)

to synthesize a compound represented by a general formula described below and having an isocyanate group in the molecule,

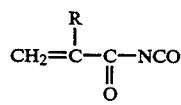

followed by a reaction of the latter compound with alcohols ($R^1OH$). This producing method is conducted by steps, because the isolation of the intermediate compounds having an isocyanate group is required. To simplify this synthetic procedure into one-step is practically difficult. Moreover, this producing method has a problem that the handling is very difficult because the intermediate compounds having an isocyanate group to be isolated are highly reactive.

SUMMARY OF THE INVENTION

Accordingly, an essential object of the present invention is to provide a process for producing unsaturated carbamic acid esters which are important compounds in the chemical materials, represented by the general formula [I]. The process is indicated by two reaction steps, but the reaction steps proceed continuously in one reaction vessel.

Another important object of the present invention is to provide a manufacturing method for unsaturated carbamic acid esters in which handling of the starting materials and reaction products are made easy.

In accomplishing these and other objects, according to one preferred embodiment of the present invention, there is provided a process for producing unsaturated carbamic acid esters represented by the following general formula of

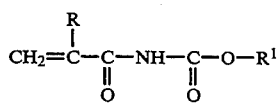
[I]

(wherein R denotes a hydrogen atom or a lower alkyl group and $R^1$ denotes a residue obtained by subtracting a hydroxyl group from a monohydric alcohol), wherein the unsaturated amide compounds represented by the general formula of

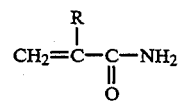
(1)

(wherein R denotes a hydrogen atom or a lower alkyl group) are allowed to react with metallic bases in inert solvents, followed by the reaction with the halogenated formic acid esters represented by the following general formula:

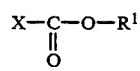
(2)

(where X denotes a halogen atom and $R^1$ denotes a residual group obtained by eliminating a hydroxyl group from a monohydric alcohol)

The present invention also provides a process for producing unsaturated carbamic acid esters represented by the general formula [I], wherein urethane derivatives represented by the general formula of

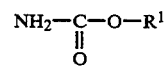
(3)

(where $R^1$ denotes the same meaning as the ones in the above-described formula) are Allowed to react with metallic bases in inert solvents, followed by the reaction with the unsaturated acid halides represented by the following general formula:

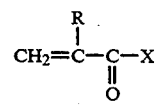
(4)

(where R and X denote the same meanings as the ones in the above-described formulae)

DETAILED DESCRIPTION OF THE INVENTION

The present invention will be described in detail hereinafter starting with Process 1.

Process 1

The unsaturated amides which are the starting materials of the processes in the present invention are commercially available and are represented by the following general formula:

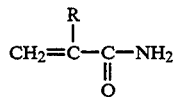 (1)

(where R denotes hydrogen or a lower alkyl group) In the formula, R preferably denotes hydrogen or a lower alkyl group having 2 to 5 carbon atoms, more preferably hydrogen or a methyl group. Typical examples of the unsaturated amide compounds are acrylamide, methacrylamide, and the like.

First, the above-mentioned unsaturated amide compounds are allowed to react with the metallic bases in the inert solvents, thereby forming the metal salts of the unsaturated amides. Metallic bases are recognized to include metallic compounds which exhibit basic properties or basic metals per se. The metallic bases include hydroxides (e.g. potassium hydroxide, sodium hydroxide, calcium hydroxide, magnesium hydroxide and aluminum hydroxide), carbonates (e.g. sodium carbonate and calcium carbonate), hydrides (e.g. sodium hydride and calcium hydride), alkylates (e.g. methyl lithium and n-butyl lithium), alkoxide compounds (e.g. sodium alkoxide and lithium alkoxide) and metals (e.g. sodium, lithium and potassium). These compounds can be used alone, or they are used as a mixture. The amount of the compounds used for the reactions is not limited, but it is in the range of 1 to 10 equivalent and preferably in the range of 2 to 5 equivalent. The inert solvents used for the reactions are not limited unless they have any effects on the reactions. Typical examples of the solvents include aliphatic hydrocarbons such as pentane, hexane and heptane; aromatic hydrocarbons such as benzene, toluene and xylene; alicyclic hydrocarbons such as cyclohexane, methyl cyclohexane and decalin; petroleum solvents such as petroleum ether and petroleum benzine; halogenated hydrocarbons such as carbon tetrachloride, chloroform and 1,2-dichloroethane; ethers such as ethyl ether, isopropyl ether, anisole, dioxane and tetrahydrofurane (THF); ketones such as acetone, methyl ethyl ketone, methyl isobutyl ketone, cyclohexanone, acetophenone and isophorone; esters such as ethyl acetate and butyl acetate; acetonitrile; dimethyl formamide (DMF); and dimethyl sulfoxide. These solvents are used alone or in the form of the mixed solvent. Preferred solvents to be used in this invention have a dielectric constant in the range of 3 to 40, examples of which are THF, dioxane, methyl isobutyl ketone, dichlorobenzene and DMF. The reactions are made to proceed in the temperature range from $-10°$ C. to $120°$ C. for 0.5 to 10 hours. The metal salts of the unsaturated amides are possible to be isolated. Since the order for mixing between the isolated metal salts of the unsaturated amides and acid chlorides is not limited, it is preferable for the continuous processing that the reactions are made to proceed by adding the halogenated formic acid ester (2) to the reaction solution without isolating the salts of the unsaturated amides.

The halogenated formic acid ester represented by the following general formula:

 (2)

(where X denotes a halogen atom, preferably chlorine or bromine, and $R^1$ denotes the residual group in which a hydroxyl group is eliminated from a monohydric alcohol) is obtained from the reaction of phosgene with alcohols ($R^1OH$). In Formula (2), $R^1$ denotes for example alkyl, cycloalkyl, allyl, aralkyl, alkaryl, alkenyl, and alkynyl (carbon numbers of these groups are in the range of 1 to 27 and 48) groups and their halogen substituents. $R^1$ also includes alkyl, cycloalkyl, allyl, aralkyl, alkaryl, alkenyl and alkynyl groups having carbon number of 1 to 27 and molecular weight of 15 to 800, which are replaced with various kinds of substituents directly or through carbonyl, ether or thioether groups.

Typical examples of the applicable halogenated formic acid esters include metyl chloroformate, propyl chloroformate, butyl chloroformate, isobutyl chloroformate, 2-ethylhexyl chloroformate, sec-butyl chloroformate, 2-methoxyethyl chloroformate, 2-ethoxyethyl chloroformate, 2-butoxyethyl chloroformate, phenoxyethyl chloroformate, butoxyethoxyethyl chloroformate, methoxybutyl chloroformate, allyl chloroformate, propargyl chloroformate, cinnamyl chloroformate, 2-chloroethyl chloroformate, 1-chloroethyl chloroformate, trichloromethyl chloroformate, benzyl chloroformate, acetoxymethyl chloroformate, methoxycarbonylmethyl chloroformate, tetrahydrofurfuryl chloroformate, ethyl chloroformate.

The reaction temperatures of the above-described reactions are not limited, but they are usually in the range of $-20°$ to $100°$ C., preferably $0°$ to $50°$ C. Reaction times are difficult to specify because they depend on the reaction temperatures and reactivity of the reagents used for the reactions. Preferred reaction time is in the range of 0.5 to 15 hours, and further preferably in the range of 1 to 7 hours. Reaction temperature of $100°$ C. or more tends to cause side reactions and too low reaction temperature is not preferable since reaction rate is lowered.

The above halogenated formic acid esters (2) and the unsaturated acid halides to be described in the following Process 2 react with metal bases vigorously. Accordingly, simultaneous mixing of these halogenated compounds and metallic bases with the amide compounds are difficult; the reaction yields will be lowered when these three kinds of compounds are mixed at the same time.

Polymerization inhibitors can be added in the reaction mixtures to avoid undesirable polymerizations at the terminal double bonds. Examples of the polymerization inhibitors include hydroquinone, p-methoxyphenol, 2,6-di-t-butyl-4-methylphenol, 4-t-butylcatechol, bis-dihydroxybenzyl benzene, 2,2'-methylenebis(6-t-butyl-3-methylphenol), 4,4'-butylidenebis(6-t-butyl-3-methylphenol), 4,4'-thiobis(6-t-butyl-3-methylphenol), p-nitrosophenol, diisopropylxantogen sulfide, N-nitrosophenylhydroxylamine ammonium salt, 1,1-diphenyl-2-picrylhydrazine, 1,3,5-triphenylpherdazyl, 2,6-di-t-butyl-α-(3,5-di-butyl-4-oxo-2,5-cyclohexanediene-1-ilidene-p-trioxy, 2,2,6,6-tetramethyl-4-piperidone-1-oxyl, dithiobenzoylsulfide, p,p'-ditolyltrisulfide, p,p'-ditolyltetrasulfide, dibenzyltetrasulfide, tetraethyltiuramdisulfide and phenothiazine.

The products are purified by the conventional method to obtain the crystalline or oily compounds.

Process 2

The second process in the present invention is characterized in that the urethane derivatives represented by the general formula:

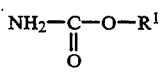

(where $R^1$ denotes the same meaning as the ones in the above-described formulae) are allowed to react with the metallic bases in the inert solvents, followed by the reaction with the unsaturated acid halides represented by the following formula.

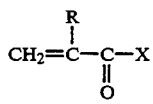

(where R and X denote the same meanings as the ones in the above-described formulae)

The urethane derivatives used in the present invention are derived from the reactions among ammonia, phosgene and alcohols. Examples of these urethane derivatives include ethyl carbamate, propyl carbamate, butyl carbamate, sec-butyl carbamate, butoxyethyl carbamate and ethoxyethyl carbamate.

The unsaturated acid halides represented by the general formula (4) include acrylic acid halide, methacryl acid halide, and the like, and the preferable halogen atom is chlorine or bromine.

As are described in Process 1, the above unsaturated acid halides are allowed to react with the urethane derivatives in the presence of the metallic bases in the inert solvents. The reaction conditions are identical with those described in Process 1.

The carbamic acid esters manufactured by the methods in the present invention are useful for starting compounds or intermediates of various kinds of materials. They are particularly important as monomers for synthetic polymer materials.

Thus, the manufacturing methods disclosed in the present invention make it possible to produce the unsaturated carbamic acid esters in industrial mass-production scale with simple manufacturing process, providing one step method for the synthetic procedure instead of the conventional two step process. Handling of the starting materials and final products is made easy.

EXAMPLES

Embodiments of the present invention will be described further referring to the examples. It is not intended that the scope of the present invention appended hereto be limited to the description as set forth herein, but rather it is understood that various other modifications will be apparent to and can be readily made by those skilled in the art without departing from the scope and spirit of this invention.

Example 1

In 41 g of dioxane, 2.5 g of methacrylamide and 1.18 g of NaOH were dissolved and the solution was stirred for 1.0 hour at the temperature of 25° to 27° C. Then, 4.0 g of ethyl chloroformate was dissolved in 10 g of dioxane and the solution was added to the reaction mixture at once. After stirring the solution for 15 minutes, water was added thereto and the solution was neutralized by adding conc. hydrochloric acid and filtered. The filtrate was extracted with chloroform and the extract was evaporated in vacuo. The crude product was subjected to column chromatography for purification, thereby obtaining 0.841 g of ethyl N-methacryloylcarbamate. Melting point (mp.) of the compound was 73°-74° C.

Example 2

In 52 g of dioxane, 12.5 g of methacrylamide and 1.0 g of sodium ethoxide (NaOEt) were dissolved and the solution was stirred for 20 minutes at the temperature of 27° C. Then, 4.0 g of ethyl chloroformate acid was dissolved in 2 g of dioxane and the solution was added in two portions into the above reaction solution. After leaving it for one day, the solution was neutralized with conc. hydrochloric acid and was extracted with chloroform. The extract was evaporated in vacuo. The crude product was subjected to column chromatography, thereby obtaining 0.44 g of ethyl N-methacryloylcarbamate. Melting point of the compound was 73°-74° C.

Example 3

In 200 g of dioxane, 4.26 g of methacrylamide and 6.37 g of potassium t-butoxide were dissolved and the solution was stirred for 60 minutes at 60° C. Then, 5.43 g of ethyl chloroformate was dissolved in 50 g of dioxane and the solution was added dropwise to the reaction mixture in 2 hours. After removing tetrahydrofurane in vacuo, 1000 g of water was added to the residue and the solution was extracted with 500 ml of ethyl acetate. The extract was evaporated in vacuo. The crude product was subjected to column chromatography, thereby obtaining 1.0 g of ethyl N-methacryloylcarbamate. Melting point of the product was 73°-74° C.

Example 4

In 100 g of dioxane, 10 g of methacrylamide and 14.4 g of sodium hydroxide were dissolved and the solution was stirred for 30 minutes at 25°-27° C. Then, 16.6 g of ethyl chloroformate was dissolved in 30 g of dioxane and the solution was added dropwise to the reaction mixture in 3 hours while keeping the reaction temperature of 25° to 30° C. After stirring the solution for 20 minutes, water was added thereto and the solution was neutralized with conc. hydrochloric acid. The solution was extracted with chloroform and the extractant was evaporated in vacuo. The crude product was subjected to NMR assay and 17.2 g of ethyl N-methacryloylcarbamate was isolated.

Example 5

After washing 2.5 g of sodium hydride with hexane, 10 g of dioxane was added to the residue. Then, 5.0 g of methacrylamide was dissolved in 32 g of dioxane and the solution was added dropwise to the first dioxane solution. After stirring the solution for 1.5 hours, 2.36 g of NaOH was added. A solution of 6.98 g of ethyl chloroformate in 10 g of dioxane was added dropwise to the reaction mixture in about 3 hours while keeping the reaction temperature at 25°-27° C. After stirring the solution for 30 minutes, water was added thereto and the solution was neutralized with hydrochloric acid. The solution was extracted with chloroform and the extractant was evaporated in vacuo. The crude product was subjected to NMR assay and 7.3 g of ethyl N-methacryloylcarbamate was isolated.

Example 6

After washing 7.1 g of sodium hydride with hexane, 100 g of dioxane was added to the residue. Then, 15.0 g of methacrylamide was dissolved in 32 g of dioxane and the solution was added dropwise to the first solution. After stirring it for 2 hours, 9.56 g of ethyl chloroformate was dissolved in 30 g of dioxane and the solution was added dropwise to the reaction mixture in about 3 hours while keeping the reaction temperature at 25°-27° C. After stirring the solution again for 30 minutes, water was added thereto and the solution was neutralized with hydrochloric acid. The solution was filtered and extracted with chloroform. The extract was evaporated in vacuo. The crude product was subjected to NMR assay and 13.7 g of ethyl N-methacryloylcarbamate (in acid chloride standard) was isolated.

Example 7

After washing 2.0 g of sodium hydride with hexane twice, 10 g of dioxane was added to the residue. A solution of 4.28 g of methacrylamide in 34 g of dioxane was added dropwise to the first solution and the mixed solution was stirred for 2 hours. The resultant slurry was filtered and the filtrate was evaporated in vacuo, obtaining sodium salt of the amide [IR(cm$^{-1}$) 3400, 3190, 1660, 1600, 1480, 1450, 1410, 1240, 1050, 930, 850, 620; $^1$H NMR (DMSO) (ppm) C$\underline{H}_3$ C$\underline{H}_3$ 5.41, 4.83 C$\underline{H}_2$=C, 1.8 CH$_2$=C. Formation of methacrylamide salt was confirmed from the observation that the broad absorption band at 1450 cm$^{-1}$ in IR spectra is absent in the starting material and NMR absorption frequencies of the olefin parts of the molecule shift to the higher magnetic field by 0.3 and 0.7 ppm. The salt was re-dispersed in 20 g of dioxane and a solution of 5.5 g of ethyl chloroformate in 20 g of dioxane was added dropwise to the slurry in 3 hours at 20° C. The crude product was evaporated in vacuo and the residue was purified by column chromatography, thereby obtaining 3.1 g of ethyl n-methacrylolycarbamate.

Example 8–21

The unsaturated carbamic acid esters were synthesized by using the similar method in Example 1 from the starting materials in Table 1 using the quantity of the materials as are listed in the table. The results (the products and yields) are shown in Table 1.

Example 22

To the solution of 8.9 g of ethyl carbamate in 100 g of THF, 11.2 g of potassium t-butoxide was mixed and the reaction mixture was stirred for 1 hour at 60° C. The resulting slurry was added dropwise to the solution of 5.43 g of methacryloyl acid chloride in 50 g of THF heated at 60° C. in 2 hours. After removing THF by vacuum evaporation, the residue was extracted with 1000 ml of water and 500 ml of ethyl acetate. The organic phase was concentrated in vacuo and the residue was subjected to column chromatography for purification, thereby isolating 1.0 g of ethyl methacryloylcarbamate.

Example 23

To the solution of 8.9 g of ethyl carbamate in 50 g of o-xylene, a slurry of 2.2 g of NaH in 20 g of xylene was added dropwise in 30 minutes, followed by stirring for additional 3 hours at 50° C. Then a solution of 10.5 g of methacryloyl chloride in 30 g of xylene was added dropwise to the reaction mixture and the solution was stirred for 1 hour at 60° C. The resultant white precipitate were filtered off and the filtrate was concentrated. The residue was subjected to column chromatography for purification, thereby obtaining 6.1 g of ethyl N-methacryloylcarbamate.

TABLE 1

| Example | Kind of amide | Amount of amide | Kind of acid chloride | Amount of acid chloride | solvent | Kind of base | Amount of base | Product | Yield | m.p. |
|---|---|---|---|---|---|---|---|---|---|---|
| 8 | Methacrylamide | 3.0 g | chloroformic acid 2-ethylhexyl ester | 8.1 g | Dioxane | Sodium ethoxide | 4.79 g | $CH_2=C(CH_3)-C(=O)-NH-C(=O)-O-CH_2CH(C_2H_5)CH_2CH_2CH_2CH_3$ | 2.5 g | Viscosity 800 cp. |
| 9 | Methacrylamide | 2.0 g | chloroformic acid isopropyl ester | 3.44 g | THF | Sodium ethoxide | 3.20 g | $CH_2=C(CH_3)-C(=O)-NH-C(=O)-O-CH(CH_3)CH_3$ | 2.0 g | 68–69 |
| 10 | Methacrylamide | 2.0 g | chloroformic acid isobutyl ester | 4.28 g | Dioxane | Sodium ethoxide | 3.20 g | $CH_2=C(CH_3)-C(=O)-NH-C(=O)-O-CH_2-CH(CH_3)-CH_3$ | 2.1 g | 41–43 |
| 11 | Methacrylamide | 2.0 g | chloroformic acid benzyl ester | 4.00 g | Dioxane | Sodium ethoxide | 3.2 g | $CH_2=C(CH_3)-C(=O)-NH-C(=O)-O-CH_2-C_6H_5$ | 2.5 g | 109–110 |
| 12 | Methacrylamide | 2.0 g | chloroformic acid propyl ester | 3.08 g | Dioxane | Potassium t-butoxide | 5.3 g | $CH_2=C(CH_3)-C(=O)-NH-C(=O)-O-CH_2CH_2CH_3$ | 3.0 g | 68–69 |
| 13 | Methacrylamide | 2.0 g | chloroformic acid propalgyl ester | 3.3 g | Dioxane | Potassium t-butoxide | 5.3 g | $CH_2=C(CH_3)-C(=O)-NH-C(=O)-O-CH_2-C\equiv CH$ | 1.1 g | 92–94 |
| 14 | Methacrylamide | 2.0 g | chloroformic acid allyl ester | 3.13 g | DMF | Potassium t-butoxide | 5.3 g | $CH_2=C(CH_3)-C(=O)-NH-C(=O)-O-CH_2-CH=CH_2$ | 2.5 g | 43.5 |
| 15 | Methacrylamide | 12.5 g | chloroformic acid ethoxyethyl ester | 22.5 g | Dioxane | Sodium ethoxide | 30 g | $CH_2=C(CH_3)-C(=O)-NH-C(=O)-O-CH_2-CH_2-OC_2H_5$ | 10.0 g | 91–92 |
| 16 | Methacrylamide | 12.5 g | chloroformic acid butoxyethyl ester | 26.7 g | Methyl-isobutyl ketone | Sodium ethoxide | 10 g | $CH_2=C(CH_3)-C(=O)-NH-C(=O)-O-CH_2CH_2O-C_4H_7$ | 15.3 g | 27–28 |

TABLE 1-continued

| Example | Kind of amide | Amount of amide | Kind of acid chloride | solvent | Amount of acid chloride | Kind of base | Amount of base | Product | Yield | m.p. |
|---|---|---|---|---|---|---|---|---|---|---|
| 17 | Methacrylamide | 12.5 g | chloroformic acid acetylmethyl ester | THF | 21.6 g | Sodium ethoxide | 20 g | 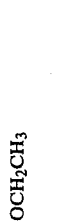 | 10.0 g | 84–86 |
| 18 | Methacrylamide | 12.5 g | chloroformic acid methoxycarbonyl methyl ester | Diethyl ether | 22.5 g | Sodium ethoxide | 20 g |  | 14.0 g | 80–82 |
| 19 | Methacrylamide | 12.5 g | chloroformic acid tetrahydro-furfuryl ester | Dioxane | 36.5 g | Sodium ethoxide | 30 g |  | 11.0 g | 68–70 |
| 20 | Acrylamide | 10.4 g | chloroformic acid ethyl ester | Dioxane | 13.3 g | Sodium ethoxide | 20 g |  | 10.0 g | 68–71 |
| 21 | Acrylamide | 10.4 g | chloroformic acid butoxyethyl ester | Dioxane | 20.3 g | Sodium ethoxide | 20 g |  | 10.0 g | |

What is claimed is:

1. A process for producing unsaturated carbamic acid esters represented by the following general formula of

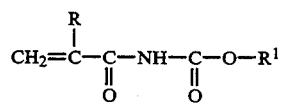

which comprises reacting urethane derivatives represented by the general formula of

with metallic bases selected from the group consisting of metallic hydroxides, metallic carbonates, metallic hydrides, metallic alkylates, metallic alkoxide compounds and mixtures thereof in inert solvents, wherein the metal of the metallic base is selected from the group consisting of sodium, potassium, calcium, magnesium, aluminum, lithium and a mixture thereof, which reaction is followed by the reaction with unsaturated acid halides represented by the following general formula:

wherein R denotes a hydrogen atom or a lower alkyl group, $R^1$ denotes alkyl, cycloalkyl, allyl, aralkyl, alkaryl, alkenyl or alkynyl groups having carbon numbers of 1 to 27 and 48, which may be substituted by halogen or may be substituted by a substituent directly or through carbonyl, ether or thioether groups and X denotes a halogen atom.

2. The process according to claim 1 wherein said urethane derivatives are selected from ethyl carbamate, propyl carbamate, butyl carbamate, sec-butyl carbamate, butoxyethyl carbamate and ethoxyethyl carbamate.

3. The process according to claim 1 wherein said metallic bases are present in an amount within the range of 1 to 10 equivalent based on one equivalent of the unsaturated urethane derivatives.

4. The process according to claim 1 wherein said inert solvents have a dielectric constant within the range of 3 to 40.

5. The process according to claim 4 wherein said inert solvents are selected from tetrahydrofuran (THF), dioxane, methyl isobutyl ketone, dichlorobenzene and dimethyl formamide (DMF).

6. The process according to claim 1 wherein the reaction between the urethane derivatives (3) and the metallic bases is conducted at a temperature of $-10°$ to $120°$ C. for 0.5 to 10 hours.

7. The process according to claim 1 wherein said unsaturated acid halides are added without isolating the reaction product between the urethane derivatives (3) and the metallic bases.

8. The process according to claim 1 wherein said unsaturated acid halides are selected from acryloyl halide and methacryloyl halide.

9. The process according to claim 1 wherein the reaction of the unsaturated acid halides is conducted $-20°$ to $100°$ C. for 0.5 to 15 hours.

10. The process according to claim 1, wherein $R^1$ denotes alkyl, cycloalkyl, allyl, aralkyl, alkaryl, alkenyl or alkynyl groups having carbon numbers of 1 to 27 and 48 and having halogen substituents.

11. The process according to claim 1, wherein $R^1$ denotes alkyl, cycloalkyl, allyl, aralkyl, alkaryl, alkenyl or alkynyl groups having carbon numbers of 1 to 27 and 48, and having a substituent group which is bonded directly to said $R^1$ group or through carbonyl, ether or thioether groups.

12. The process according to claim 1, wherein the inert solvent is an organic solvent.

* * * * *